(12) United States Patent
Benedetti et al.

(10) Patent No.: US 7,718,407 B2
(45) Date of Patent: May 18, 2010

(54) PROCESS FOR THE PREPARATION OF VITAMIN K2

(75) Inventors: Alberto Benedetti, Cernusco Sul Naviglio (IT); Simona Daly, Monza (IT); Roberto Xaiz, Monza (IT); Hermes Pagani, Sesto San Giovanni (IT)

(73) Assignee: GNOSIS S.p.A., Desio (IR)

( * ) Notice: Subject to any disclaimer, the term of this patent is extended or adjusted under 35 U.S.C. 154(b) by 0 days.

(21) Appl. No.: 11/635,768

(22) Filed: Dec. 8, 2006

(65) Prior Publication Data

US 2007/0154998 A1 Jul. 5, 2007

(30) Foreign Application Priority Data

Dec. 29, 2005 (EP) ................... 05425932

(51) Int. Cl.
*C12P 7/66* (2006.01)
(52) U.S. Cl. .............. 435/133; 435/243; 435/252.5
(58) Field of Classification Search ............ None
See application file for complete search history.

(56) References Cited

U.S. PATENT DOCUMENTS 3,725,200 A 4/1973 Watanabe et al.
5,024,937 A * 6/1991 Penticoff et al. ............ 435/41
5,685,128 A * 11/1997 Chum et al. ................. 53/441
6,677,141 B2 * 1/2004 Sumi ...................... 424/93.462

FOREIGN PATENT DOCUMENTS

EP 0 320 685 A1 6/1989
JP 3272657 12/1991

OTHER PUBLICATIONS

Sato et al., Journal of Industrial Microbiology& Biotechnology, 2001, vol. 26, p. 115-120.*
Schallmey et al., Can. J. Microbiol. Jan. 2004, vol. 50, 1-14.*
Ozcengiz et al., Journal of Industrial Microbiology, 1990, vol. 6, p. 91-100.*
Schonert et al., Res. Microbiol., 1999, vol. 150, p. 167-177.*
Tsukamoto et al., Biosci. Biotechnol. Biochem., 2001, vol. 65 p. 2007-2015.*
Flückiger-Isler et al. , J Nutr., 1994, vol. 14, p. 1647-1653.*
Schönert et al. (Res. Microbiol., 1999, vol. 150, p. 167-177.*
Schisler et al., Phytopathology, 2004, vol. 94 No. 11, p. 1267-1271.*
Sato T et al: "Production of Menaquinone (Vitamin K2)-7 by *Bacillus subtilis*"; Journal of Bioscience and Bioengineering, Elsevier, Amsterdam, NL., vol. 91, No. 1, Jan. 9, 2001, pp. 16-20.
European Search Report completed Jun. 28, 2006 in EP 05 42 5932.

* cited by examiner

*Primary Examiner*—L Blaine Lankford
*Assistant Examiner*—Kade Ariani
(74) *Attorney, Agent, or Firm*—Arent Fox LLP

(57) ABSTRACT

A process for the preparation of vitamin K2 (MK-7) comprising the culture of *Bacillus subtilis* mutant strain GN13/72-DSM 17766 deposited on Dec. 5, 2005 at the DSMZ.

7 Claims, No Drawings

PROCESS FOR THE PREPARATION OF VITAMIN K2

The present invention concerns the fermentative production of vitamin K2 (menaquinone-7: MK-7), using a *Bacillus* microorganism.

The invention concerns a mutant of the microorganism *Bacillus subtilis* deposited under the Budapest Treaty, which is able to produce MK-7 in high amounts, under specific culture conditions.

PRIOR ART

Vitamin K is an essential cofactor for the formation of γ-carboxyglutamic acid (Gla) residues in proteins (Olson, R. E., 1984[1]-Suttie, J. W., 1985[2]). The Gla-containing proteins bind calcium ions and influence, for example, blood coagulation and tissue calcification (e.g., osteocalcin found in bone tissues) (Hauschka P. V. et al. 1978[3]-Price, P. A. et al., 1976[4]). Vitamin K deficiency has been implicated in several clinical ailments such as intracranial hemorrhage in newborn infants (Ferland, G. et al., 1993[5]-Shearer, M. J., 1995[6]) and possible bone fracture resulting from osteoporosis (Knapen, M. H. et al., 1989[7]).

Vitamin K occurs naturally in two forms, namely, K1 (phylloquinone) in green plants and K2 (menaquinones-MK) in animals and some bacteria (Collins, M. D. et al., 1981[8]-Conly, J. M. et al. 1992[9]-Ramotar, K. et al., 1984[10]-Taber, H. 1980[11]-Watanuki, M. et al. 1972[12]), including intestinal bacteria. MK has a variable side chain length of 4-13 isoprene units. They are referred to as MK–η, where η denotes the number of isoprenoid residues. The MK are constituents of the bacterial plasma membrane and function as redox reagents in electron transport and oxidative phosphorylation systems (Taber, H. 1980-Ramotar, K. et al. 1984).

Lactic acid bacteria have been used as starter cultures to manufacture various foods and can be generally recognized as safe (GRAS), and a qualitative study has shown that some lactic acid bacteria produce MK. In many countries, the daily requirement for vitamin K is around 1 μg/kg of body weight. Rowland, B. M. and Taber, H. W. (1996)[13]-Rowland, B. et al. (1995)[14]-Taber H. W. et al. (1981)[15] have extensively studied the mechanism of MK formation in *Bacillus subtilis*. However, studies to increase production of MK by *B. subtilis* have not been reported. Tani, Y. and Sakurai, N. (1987)[16]-Tani, Y. and Taniguchi, H. (1989)[17] reported on the efficient production of MK-4, MK-5 and MK-6 by Flavobacterium and that the maximum concentration of MK produced reached 192 mg/l (Tani, Y. et al.-1989). On the other hand, industrial production of MKs with longer isoprene side chains was not reported until recently by Morishita, T. et al. (1999)[18]. In their study, 29-123 μg/l of MK-7 was produced by lactic acid bacteria. The fermented soybean "natto", whose production requires *B. subtilis*, is popular in Japan and contains an exceptionally large amount of MK (600-900 μg/100 g) (Sakano, T. et al. 1988)[19]. Since the strains of *B. subtilis* used for manufacturing natto are edible, they are among the most advantageous source of MK in the food industry.

Yoshinori Tsukamoto et al. (2001) have recovered a analogous resistant mutant of *B. subtilis* "natto" having productivity of 1719 μg/100 g dry weight. According to a number of patents or patent applications exist, some of which are listed in the following, K2 (MK-7) is produced in amounts of 1.0 μg/g dry weight or below (US 2004/043015; US 2005/0025759; US 2002/0146786; US 2001/0046697).

It has now been found, and this is the object of the present invention, a *Bacillus subtilis* mutated strain having productivity ranging from 1,000 to 25,000 ppm of dry matter, with a production cycle (from pre-seed to fermentation) of 160-200 hours, more precisely 170-185 hours. The *Bacillus subtilis* mutant GN13/72 was obtained by treatments with NTG or, alternatively, U.V. and recovered on a micronised soy meal solid medium.

The strain was deposited under the terms of the Budapest Treaty at the Deutsche Sammiung von Mikroorganismen und Zellkulturen GmbH (DSMZ), located at Mascheroder Weg 1b. D-35124 Braunschweig, Germany, on Dec. 5, 2005 under the accession number DSM 17766.

The MK-7 high-content biomass is prepared according to known fermentation techniques by means of culture media containing carbon sources (such as glucose, saccharose, glycerol, starch hydrolysate and the like); nitrogen sources (such as yeast extract or autolysate, peptones of various origin, soy meal and the like); various salts (such as potassium phosphate, sodium chloride, magnesium sulfate, manganese sulfate, zinc sulfate, and the like).

pH ranges from 6.0 to 8.5, more precisely from 6.5 to 7.8; air flow ranges from 0.1 to 2.0 vvm, more precisely from 0.2.5 to 1.0 vvm; stirring rate in the fermenter varies from 100 to 250 rpm; pressure ranges between 0.1 and 1.2 bars, more precisely between 0.25 and 1.0 bars. Fermentation is carried out in batch or fed-batch mode; conventional STR (=Stirred Tank Reactor) or CSTR (=Continuous Stirred Tank Reactor) fermenters are used.

The biomass is collected by centrifugation or microfiltration, washed twice with purified water and resuspended in purified water. The resulting creams are dried by freeze-drying or spray-drying, then packaged under vacuum.

The invention is illustrated in detail by the following examples.

EXAMPLE 1

*Bacillus subtilis* GN13/72-DSM 17766 is aerobically grown in a 30 l (geometrical) fermenter containing 20 l of "F10" fermentation medium having the following composition:

| | |
|---|---|
| Micronized soy meal | 15.00 g/l |
| Yeast extract | 1.00 g/l |
| Glycerol | 10.00 g/l |
| K$_2$HPO$_4$ | 0.05 g/l |
| NaCl | 5.00 g/l |
| pH 7.3 (±0.1) | | sterilization at 121° C. × 30 minutes

The fermenter is inoculated with 8% (1600 ml) of 16 h (±2 h) seed, whose "S3" medium has the following composition:

| | |
|---|---|
| Soy peptone | 10.00 g/l |
| Glycerol | 5.00 g/l |
| pH 7.2 (±0.1) | |

The seed was in turn inoculated with 5 ml of *B. subtilis* suspension from a slant washed with 10 ml of purified water.

| Growth conditions: | |
|---|---|
| Seed: | 3 l of shaker flask with 800 ml of medium Incubation temperature 37° C. |

-continued

Growth conditions:

| | |
|---|---|
| Fermenter: | Stirring 90 rpm |
| | Time 17 h (± 2 h) |
| | Stirring 120 rpm |
| | Air 0.6 vvm |
| | Pressure 0.25 bar |
| | Temperature 37° C. |
| | Silicon antifoam |
| | Time 144 h (± 4 h) |

The biomass obtained under said conditions was 8 (±1) g/l dry weight with MK-7 content of 1100 (±100) ppm.

EXAMPLE 2

*Bacillus subtilis* GN13/72-DSM 17766 is cultured as in Example 1, the "F12" fermentation medium having the following composition:

| | |
|---|---|
| Soy peptone | 10.00 g/l |
| Glycerol | 10.00 g/l |
| Yeast extract | 1.00 g/l |
| $K_2HPO_4$ | 0.05 g/l |
| NaCl | 5.00 g/l |

Duration of the fermentation 140 h (±2 h).

10 (±1 g) g/l dry weight are obtained with MK-7 content of 3000 (±100) ppm.

EXAMPLE 3

*Bacillus subtilis* GN13/72-DSM 17766 is cultured as in Example 1, the "F13" fermentation medium having the following composition:

| | |
|---|---|
| Soy peptone | 12.00 g/l |
| Yeast extract | 0.50 g/l |
| Dextrin | 60.00 g/l |
| $K_2HPO_4$ | 0.05 g/l |
| NaCl | 5.00 g/l |

Duration of the fermentation 140 h (±1 h).

9.0 (±1.0) g/l dry weight are obtained with MK-7 content of 7800 (±200) ppm.

EXAMPLE 4

*Bacillus subtilis* GN13/72-DSM 17766 is cultured as in Example 3, the carbon source consisting of maltodextrin instead dextrin.

Duration of the fermentation 140 h (±3 h).

8.0 (±1.0) g/l dry weight are obtained with MK-7 content of 8500 (±150) ppm.

EXAMPLE 5

*Bacillus subtilis* GN13/72-DSM 17766 is cultured as in Example 4, the antifoam agent being soybean oil.

Duration of the fermentation 144 h (±4 h).

11 (±1) g/l dry weight are obtained with MK-7 content of 11700 (±300) ppm.

EXAMPLE 6

*Bacillus subtilis* GN13/72-DSM 17766 is cultured in a 300 l fermenter, with 225 l useful volume, medium "F13", pH automatically kept at 7.2 (±0.1) with NaOH; stirring 100 rpm; air 0.5 vvm; pressure 0.3 bar; antifoam soybean oil automatically controlled.

Inoculum was 4% obtained in a seed of 30 l total with 20 l useful volume and "S3" medium (see Example 1).

Duration of the fermentation 142 h (±4 h). Obtained biomass 11 (±1.0) g/l dry weight Obtained MK-7: 15150 (±200) ppm.

EXAMPLE 7

*Bacillus subtilis* GN13/72-DSM 17766 is cultured as in Example 6. Fermentation was arrested before reaching the stationary phase. 7.0 (±1.5) g/l dry weight are obtained, with MK-7 productivity=21000 ppm. The biomass was divided into 2 parts: a part was freeze-dried to obtain a powder having 17000 (±350) ppm; the other part was spray-dried to obtain 20000 (±500) ppm.

Operative conditions of the Spray Dryer:
Inlet air temperature 200° C.
Outlet air temperature 80° C.

EXAMPLE 8

The procedure of Example 7 is followed, in which the fermentation useful volume was 2 m³. The spray-dried final product was packaged in 250 g sachets under vacuum.

LITERATURE

1. Annu. Rev. Nutr. 4:281-337.
2. Annu. Rev. Biochem. 54:459-477.
3. J. Biol. Chem. 253:9063-9068.
4. Proc. Natl. Acad. Sci. USA 73:1447-1451.
5. J. Clin. Invest. 91:1761-1768.
6. Lancet 345:229-234.
7. Ann. Int. Med. 111:1001-1005.
8. Microbiol. Rev. 45:316-354.
9. Prog. Food Nutr. Sci. 16:307-343.
10. J. Infect. Dis. 150:213-218.
11. Functions of vitamin K2 in microorganisms. Pages 177-187 in Vitamin K metabolism and vitamin K-dependent proteins. J. W. Suttie, Ed. Univ. Park Press, Baltimore, Md.
12. J. Gen. Appl. Microbiol. 18:469-472.
13. J Bacteriol 178:854-861.
14. Gene 167:105-109.
15. J Bacteriol 145:321-327.
16. Agric Biol Chem 51:2409-2415.
17. J Ferment Bioeng 67:102-106.
18. J Dairy Sci 82:1897-1903.
19. Vitamins (Japan) 62:393-398.

The invention claimed is:

1. A process for the preparation of vitamin K2 (MK-7) comprising:
   culturing *Bacillus subtilis* mutant strain GN13172-DSM 17766 in combination with a carbon source and an antifoam agent for a time sufficient to produce from 1,000 to 25,000 ppm vitamin K2 (MK-7) based on dry matter content of biomass produced by the culture.

2. The process as claimed in claim 1 wherein the carbon source used is dextrin.

3. The process as claimed in claim 1 wherein the carbon source used is maltodextrin.

4. The process as claimed in claim 1 wherein the antifoam agent used is soybean oil.

5. The process claimed in claim 1, further comprising the step of:

drying by spray-drying a biomass produced by the culturing step.

6. The process claimed in claim 5, further comprising the step of:

packaging the dried biomass under vacuum.

7. *Bacillus subtilis* GN13/72—DSM 17788.

* * * * *